US 11,478,613 B2

(12) United States Patent
Katayama et al.

(10) Patent No.: US 11,478,613 B2
(45) Date of Patent: Oct. 25, 2022

(54) CATHETER

(71) Applicant: Olympus Corporation, Hachioji (JP)

(72) Inventors: Tomofumi Katayama, Kokubunji (JP); Takayuki Hatanaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 165 days.

(21) Appl. No.: 16/710,716

(22) Filed: Dec. 11, 2019

(65) Prior Publication Data

US 2020/0114122 A1 Apr. 16, 2020

Related U.S. Application Data

(63) Continuation of application No. PCT/JP2017/022088, filed on Jun. 15, 2017.

(51) Int. Cl.
*A61M 25/01* (2006.01)
*A61M 25/06* (2006.01)

(52) U.S. Cl.
CPC .... *A61M 25/0138* (2013.01); *A61M 25/0169* (2013.01); *A61M 25/0662* (2013.01);
(Continued)

(58) Field of Classification Search
CPC .......... A61M 25/0023; A61M 25/0067; A61M 25/0074; A61M 25/008; A61M 25/0082; A61M 25/01; A61M 25/0169; A61M 25/0662; A61M 2025/0004; A61M 2025/0006; A61M 2025/0177;
(Continued)

(56) References Cited

U.S. PATENT DOCUMENTS 4,423,740 A * 1/1984 Castle .................. A61B 5/03
600/561
9,757,103 B2 9/2017 Yokota et al.
(Continued)

FOREIGN PATENT DOCUMENTS

CN 101854882 A 10/2010
JP H9-173465 A 7/1997
(Continued)

OTHER PUBLICATIONS

Sep. 19, 2017 Written Opinion Of The International Search Authority issued in Application No. PCT/JP2017/022088.
(Continued)

*Primary Examiner* — Kami A Bosworth
(74) *Attorney, Agent, or Firm* — Oliff PLC

(57) ABSTRACT

A catheter can include a catheter main body and a sheath that covers the catheter main body and can move along the longitudinal axis with respect to the catheter main body. An operating unit can be disposed at a proximal end portion of the sheath and can move the sheath and the catheter main body with respect to one another. The catheter main body can include a slit on an outer peripheral surface of a distal end portion and can extend along the longitudinal axis from a slit distal end to a slit proximal end side. An outside diameter of the distal end portion of the catheter main body is larger than an inside diameter of a distal end portion of the sheath when the distal end portion of the catheter main body is housed in the sheath.

8 Claims, 10 Drawing Sheets

(52) U.S. Cl.
CPC .............. *A61M 2025/0188* (2013.01); *A61M 2025/0681* (2013.01)

(58) Field of Classification Search
CPC ........... A61M 2025/0681; A61M 2025/09125; A61M 25/09041; A61M 2025/0024; A61M 2025/0079; A61M 2025/0096; A61M 2025/0175; A61M 2025/018; A61M 2025/0188; A61B 2017/00623; A61B 2017/22035
See application file for complete search history.

(56) References Cited

U.S. PATENT DOCUMENTS

| | | | |
|---|---|---|---|
| 10,071,231 B2 | 9/2018 | Yokota et al. | |
| 2008/0275458 A1 | 11/2008 | Bleich et al. | |
| 2009/0105653 A1* | 4/2009 | Spenser ................ | A61M 25/09 604/164.13 |
| 2013/0090624 A1* | 4/2013 | Munsinger .............. | A61F 2/958 604/500 |
| 2013/0317485 A1* | 11/2013 | Lupton ........... | A61M 25/09041 606/1 |
| 2014/0025086 A1* | 1/2014 | Rottenberg ............ | A61B 17/50 606/127 |
| 2015/0018939 A1* | 1/2015 | Colson ................... | A61F 2/243 623/2.11 |
| 2015/0142009 A1* | 5/2015 | Ahn ..................... | A61B 17/221 606/127 |
| 2016/0121083 A1 | 5/2016 | Yokota et al. | |
| 2016/0279393 A1* | 9/2016 | Anderson ........... | A61B 17/221 |
| 2017/0100582 A1* | 4/2017 | McEvoy .............. | A61N 1/3756 |
| 2017/0232237 A1 | 8/2017 | Yokota et al. | |
| 2017/0246431 A1 | 8/2017 | Yokota et al. | |
| 2019/0365206 A1 | 12/2019 | Katayama et al. | |

FOREIGN PATENT DOCUMENTS

| | | | |
|---|---|---|---|
| JP | H10-272139 | A | 10/1998 |
| JP | 2001-137351 | A | 5/2001 |
| JP | 2014-097103 | A | 5/2014 |
| JP | 2016-140630 | A | 8/2016 |
| JP | 2017-169783 | A | 9/2017 |
| WO | 2016/103897 | A1 | 6/2016 |
| WO | 2016/103900 | A1 | 6/2016 |
| WO | 2018/047340 | A1 | 3/2018 |
| WO | 2018/163410 | A1 | 9/2018 |
| WO | 2018/229925 | A1 | 12/2018 |

OTHER PUBLICATIONS

Sep. 19, 2017 International Search Report issued in Application No. PCT/JP2017/022088.
May 27, 2021 Office Action issued in Chinese Patent Application No. 201780091835.4.

* cited by examiner

CATHETER

CROSS-REFERENCE TO RELATED APPLICATION

This application is a continuation application of PCT Application No. PCT/JP2017/022088 filed on Jun. 15, 2017, which is hereby incorporated by reference in its entirety.

TECHNICAL FIELD

The disclosed technology relates to a catheter that holds a guide wire.

DESCRIPTION OF THE RELATED ART

It is known that, at a time of treatment or examination of a hollow organ of a human body, a medical instrument is introduced into the hollow organ by using a guide wire. There is a case where the guide wire itself cannot be inserted into the hollow organ when there is an obstacle such as a constriction and an occlusion in an opening portion of the hollow organ. For example, in a case where a duodenal papilla is closed firmly, it is difficult to insert the guide wire into a target hollow organ such as a bile duct and a pancreatic duct via the duodenal papilla.

A method referred to as a rendezvous technique is known as a method for dealing with such a case. In the rendezvous technique, a guide wire introduced into a bile duct or a pancreatic duct from a site other than the duodenal papilla is projected to a duodenum side from the duodenal papilla, and an end portion of the projected guide wire is retained by a medical instrument inserted into a duodenum. The guide wire retained by the medical instrument is pulled out to the outside of the body via a treatment instrument channel of an endoscope inserted into the duodenum. A stent placement or the like is performed by using the guide wire pulled out to the outside of the body.

Japanese Patent Application-JP 2016-140630 A (PTL 1), for example, discloses a medical instrument that can capture a guide wire projected from the duodenal papilla. The medical instrument includes a tubular sheath, a wire inserted in the sheath, and a distal end portion disposed at a distal end of the wire and extending along the extending direction of the wire. The distal end portion has a bending portion bending in a predetermined shape so as to be able to hook the guide wire.

In addition, as described in US Patent Application-US 2016/0121083 A (PTL 2), for example, a method is known which introduces a medical instrument holding a guide wire into the bile duct or the pancreatic duct together with a treatment instrument by pulling back the guide wire projected from the duodenal papilla to the inside of the duodenum into the bile duct or the pancreatic duct when the treatment instrument such as a stent is placed by the rendezvous technique.

In the method of introducing the medical instrument into the bile duct or the pancreatic duct by pulling back the guide wire described hereinbefore, the axis of the medical instrument and the axis of the guide wire held by the medical instrument are desirably parallel with each other when the medical instrument is inserted into the duodenal papilla. This can facilitate insertion of the medical instrument from the duodenal papilla into the bile duct or the pancreatic duct.

However, because the medical instrument described in PTL 1, for example, has the configuration of hooking the guide wire on the bending portion, a certain angle is formed between the axis of the medical instrument and the axis of the guide wire. With such a medical instrument, it may be difficult for the distal end portion in a state of hooking the guide wire on the bending portion to enter the inside of the bile duct or the pancreatic duct from the duodenal papilla.

BRIEF SUMMARY OF EMBODIMENTS

One aspect of the disclosed technology is directed to a catheter comprises a catheter main body having a longitudinal axis. A sheath covers the catheter main body and is movable along the longitudinal axis with respect to the catheter main body. An operating unit is disposed at a proximal end portion of the sheath. The operating unit is used to move the sheath and the catheter main body with respect to one another along the longitudinal axis. The catheter main body includes a slit that is formed in an outer peripheral surface of a distal end portion thereof. The slit extends along the longitudinal axis from a slit distal end to a slit proximal end side. In a direction of the longitudinal axis, the distal end of the catheter main body and the distal end of the slit coincides with one another. An outside diameter of the distal end portion of the catheter main body is larger than an inside diameter of a distal end portion of the sheath in a state in which the distal end portion of the catheter main body is housed in the sheath. The distal end portion of the catheter main body is elastically deformed by being pressed by an inner peripheral surface of the sheath. An opening width of the slit is smaller than the opening width of the slit in a state in which the distal end portion of the catheter main body projects from the distal end of the sheath.

Another aspect of the disclosed technology is directed to a catheter comprises a catheter main body having a longitudinal axis. A sheath covers the catheter main body and is movable along the longitudinal axis with respect to the catheter main body. An operating unit is disposed at a proximal end portion of the sheath and the operating unit is used to move the sheath and the catheter main body relative to one another along the longitudinal axis. The catheter main body includes a slit being formed in an outer peripheral surface of a distal end portion thereof. The slit extends along the longitudinal axis from a slit distal end to a slit proximal end side. In a direction of the longitudinal axis, the distal end of the catheter main body and the distal end of the slit coincides with one another. At least one of protruding portion is disposed on a part of an inner peripheral surface of the distal end portion of the sheath and in a state in which the distal end portion of the catheter main body is housed in the sheath, the distal end portion of the catheter main body is elastically deformed by being pressed by the protruding portion, and an opening width of the slit being smaller than the opening width of the slit in a state in which the distal end portion of the catheter main body projects from the distal end of the sheath.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 12 is a side view as viewed from the direction of an arrow XII depicted in

FIG. 11.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

In light of the circumstances described hereinbefore, it is an object of the disclosed technology to provide a catheter that can be introduced into a hollow organ easily by the rendezvous technique.

First Embodiment

A first embodiment of the disclosed technology will hereinafter be described with reference to FIGS. 1 to 6.

Figure 1:
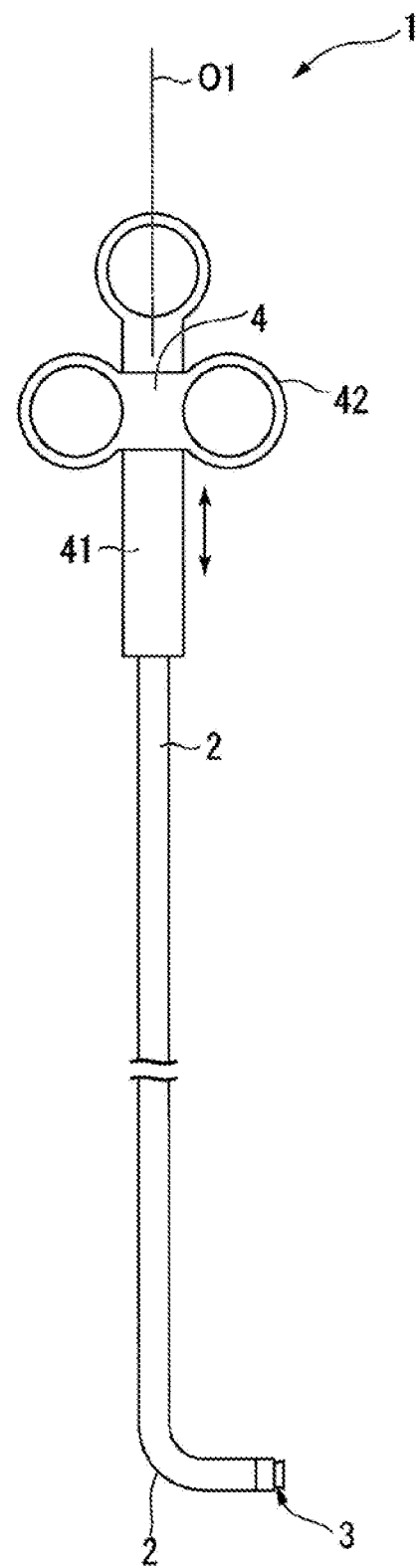
FIG. 1 is a general view depicting a catheter according to a first embodiment of the disclosed technology.
Figure 2:
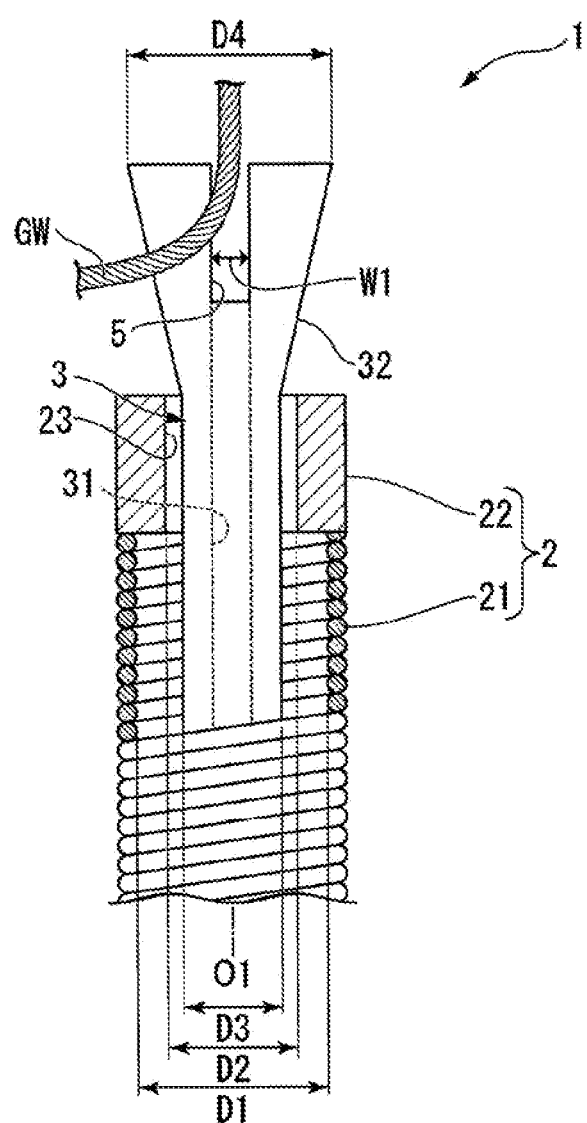
FIG. 2 is a fragmentary sectional view depicting a distal end portion of the catheter according to the first embodiment.
Figure 3:
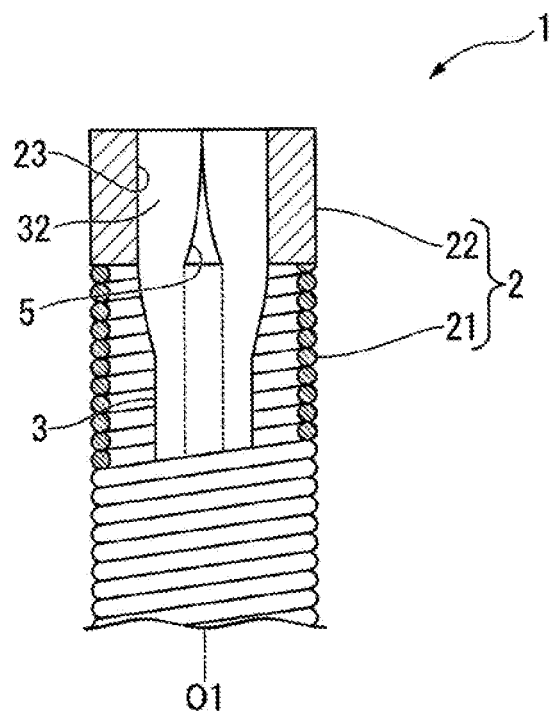
FIG. 3 is a fragmentary sectional view depicting the distal end portion of the catheter according to the first embodiment.
Figure 4:
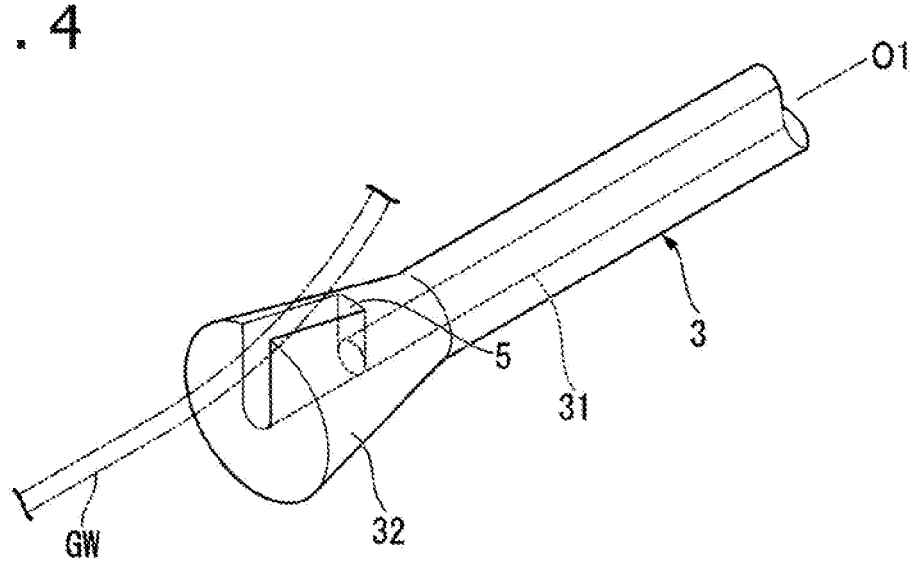
FIG. 4 is a perspective view depicting a distal end portion of a catheter main body in FIG. 2.
Figure 5:
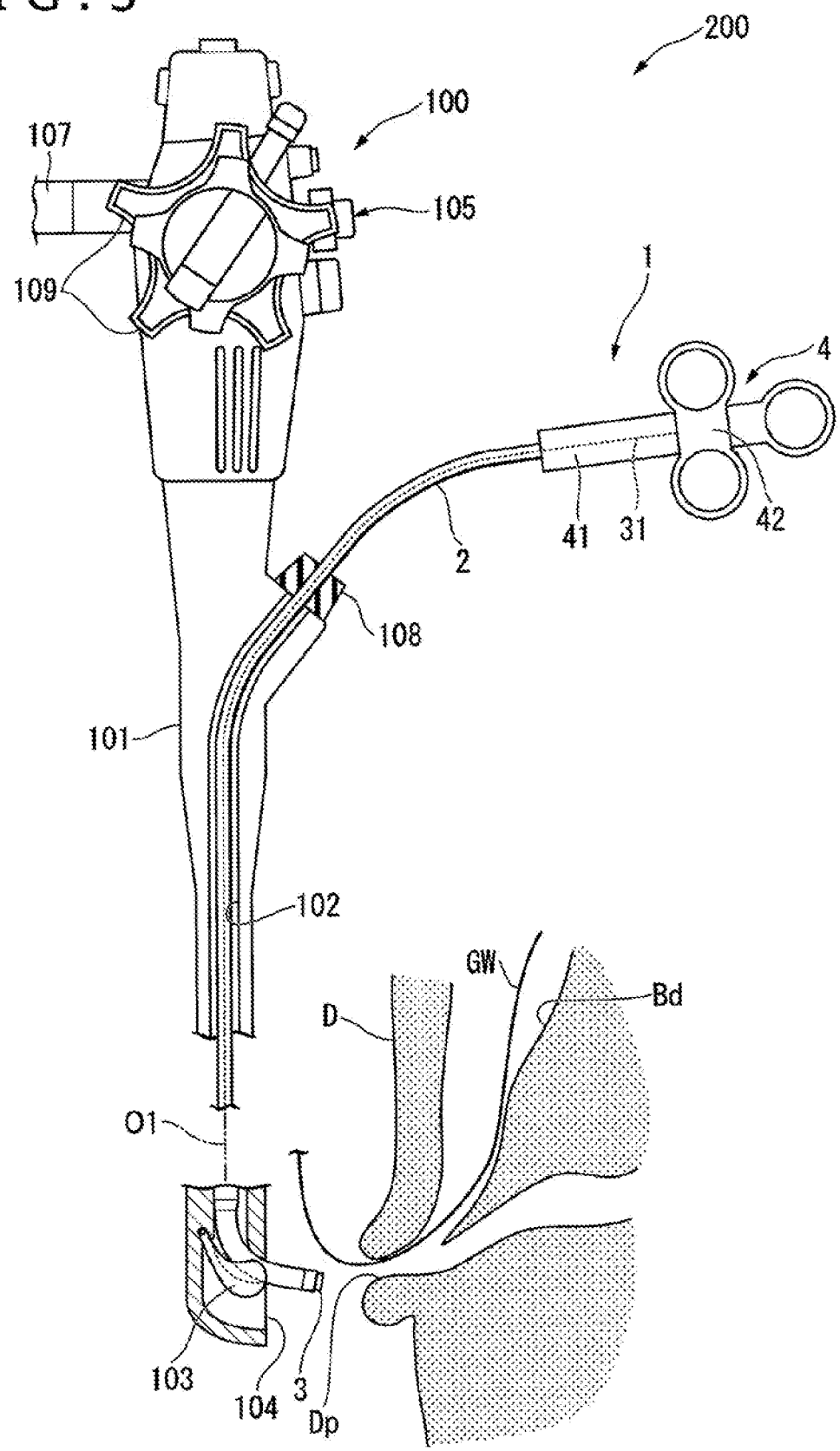
FIG. 5 is a diagram depicting an example of a procedure using the catheter in FIG. 1 and an endoscope into which the catheter is inserted.
Figure 6:
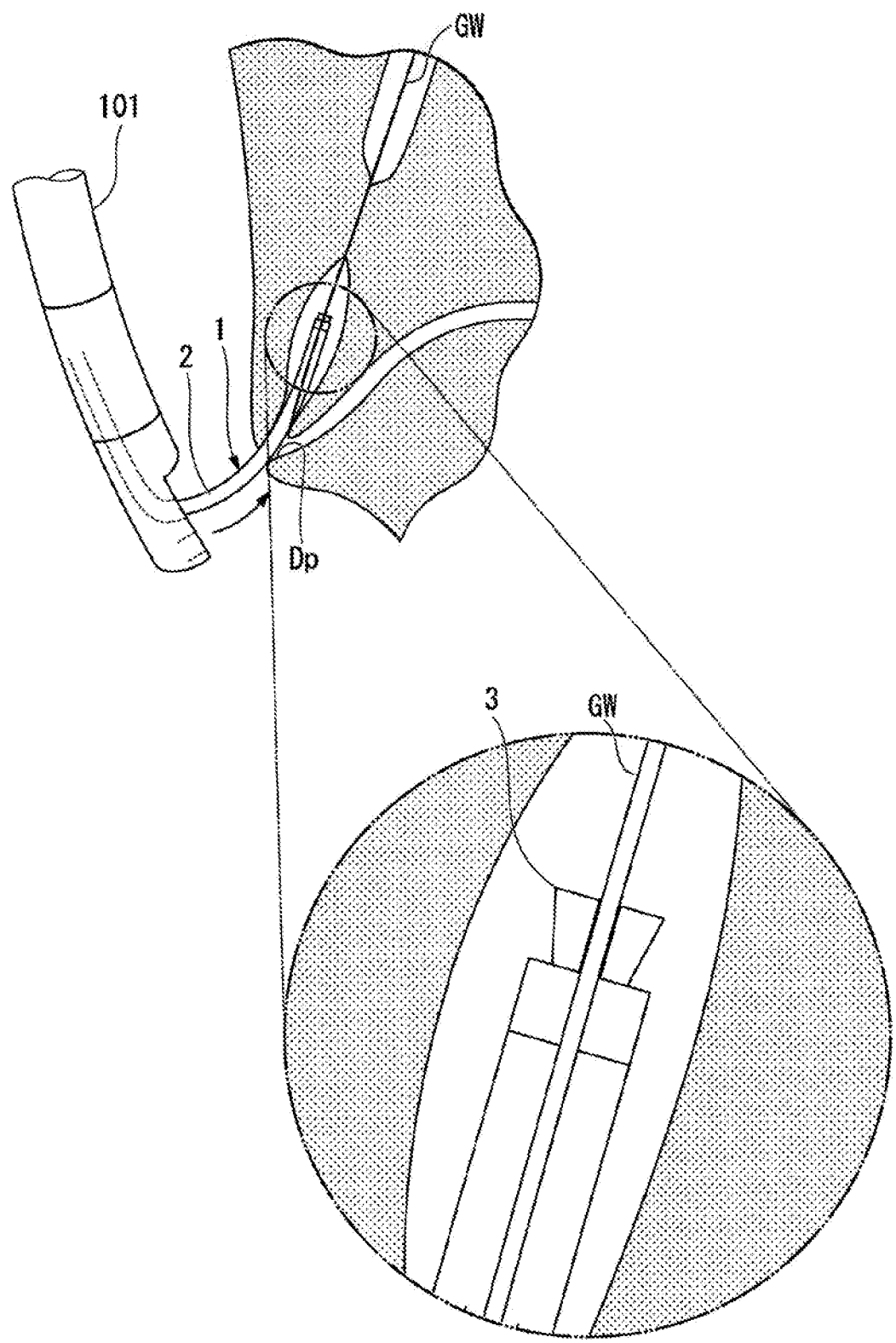
FIG. 6 is a diagram depicting the example of the procedure using the catheter in FIG. 1 and the endoscope into which the catheter is inserted.

FIG. 1 is a general view depicting a catheter 1 according to the present embodiment. FIG. 2 and FIG. 3 are fragmentary sectional views depicting a distal end portion of the catheter 1. FIG. 4 is a perspective view depicting a catheter main body. FIG. 5 and FIG. 6 are diagrams depicting an example of a procedure using the catheter 1 and an endoscope 100 into which the catheter 1 is inserted.

The catheter 1 is a medical instrument used to hold a known guide wire GW. The outside diameter of the guide wire GW is, for example, 0.6 mm. As depicted in FIG. 1, the catheter 1 includes a sheath 2, a catheter main body 3, or a long-axis member, and an operating unit 4.

As depicted in FIGS. 2 to 4, the sheath 2 is a long tubular member extending along a longitudinal axis O1. In the present embodiment, the sheath 2 includes a sheath main body 21 and a distal end member 22. The sheath main body 21 is a coil sheath extending along the longitudinal axis O1.

The distal end member 22 is a tubular member disposed at a distal end of the sheath main body 21 coaxially with the longitudinal axis O1. The distal end member 22 is fixed to the distal end of the sheath main body 21. The distal end member 22 has higher stiffness than the sheath main body 21. The distal end member 22 is, for example, formed of a metal such as stainless steel. An insertion hole 23 penetrating in the direction of the longitudinal axis O1 is formed in the distal end member 22. As depicted in FIG. 2, an inside diameter D2 of the insertion hole 23, or an inside diameter of the distal end member 22, is smaller than an inside diameter D1 of the sheath main body 21.

The catheter main body 3 is a long tubular member having flexibility. The catheter main body 3 has a lumen 31 extending along the longitudinal axis O1 and opening on a distal end side. The lumen 31 is used to feed a liquid such as a contrast medium or to insert a guide wire. The catheter main body 3 is, for example, formed by a resin such as PTFE (polytetrafluoroethylene).

As depicted in FIG. 2 and FIG. 4, a slit 5 is formed in an outer peripheral surface of a distal end portion of the catheter main body 3. The slit 5 is formed so as to extend along the longitudinal axis O1 from a distal end to a proximal end side of the catheter main body 3. In a longitudinal-axis direction, the distal end of the catheter main body 3 and a distal end of the slit 5 coincide with each other. In the present embodiment, the slit 5 is formed so as to communicate with the lumen 31 from one position in a circumferential direction of the outer peripheral surface of the catheter main body 3 (see FIG. 4). As depicted in FIG. 2, preferably, an opening width W1 of the slit 5 in the circumferential direction of the catheter main body 3 is sufficiently larger than a diameter of the guide wire GW to be held. Incidentally, the opening width W1 of the slit 5 may be slightly smaller than the diameter of the guide wire GW. In this case, the guide wire GW can be inserted by press-fitting the guide wire GW into the slit 5.

The distal end portion of the catheter main body 3 has a tapered portion 32, or an inclined portion, which is increased in diameter from the proximal end side to the distal end. Because the catheter main body 3 has the tapered portion 32, an outside diameter D4 of the distal end of the catheter main body 3 is larger than an outside diameter D3 in a region from a proximal end portion of the catheter main body 3 to a proximal end of the tapered portion 32. The outside diameter D4 is larger than the inside diameter D2 of the insertion hole 23 of the distal end member 22. The tapered portion 32 has stiffness to such a degree as to be elastically deformable by an external force. Hence, as depicted in FIG. 3, when the distal end member 22 relatively moves to a distal end portion side of the catheter main body 3, the tapered portion 32 is elastically deformed by being pressed by an inner peripheral surface of the insertion hole 23. The distal end portion of the catheter main body 3 can be thereby housed in the distal end member 22. At this time, the opening width W1 of the slit 5 is reduced by the elastic deformation of the distal end portion of the catheter main body 3 due to pressing. On the other hand, as depicted in FIG. 2, no external force is applied to the tapered portion 32 in a state in which the distal end portion of the catheter main body 3 projects from the distal end member 22 on a distal end side. The tapered portion 32 is therefore in an opened state in which the slit 5 is opened. The slit 5 can be opened and closed when the outside diameter D4 of the distal end of the catheter main body 3 is larger than the inside diameter D2 of the distal end member 22 in at least a region from the distal end to a proximal end of the slit 5.

Incidentally, an external shape of the inclined portion in a cross section of the inclined portion is not limited to a perfect circle and may be a non-perfect circle (for example, an ellipse). In a case where the external shape of the inclined portion in the cross section of the inclined portion is an ellipse, it suffices for the outside diameter at the distal end portion of the catheter main body 3 (major axis of the ellipse) to be larger than the inside diameter D2 of the distal end member 22.

The outside diameter D3 of the catheter main body 3 is set smaller than the inside diameter D1 of the sheath main body 21 and the inside diameter D2 of the insertion hole 23 of the distal end member 22. Therefore, a region of the catheter main body 3 which region has the outside diameter D3 can easily advance or retreat in the sheath main body 21 and the distal end member 22

As depicted in FIG. 2, the proximal end of the slit 5 is located on a distal end side as compared to the proximal end of the tapered portion 32. The proximal end of the slit 5 does not necessarily need to be located on the distal end side as compared to the proximal end of the tapered portion 32. For example, the proximal end of the slit 5 may be located at a position equal to the position of the proximal end of the tapered portion 32 in the direction of the longitudinal axis O1, or may be located on a proximal end side as compared to the proximal end of the tapered portion 32.

As depicted in FIG. 1, the operating unit 4 is disposed at a proximal end portion of the sheath 2. The operating unit 4 includes an operating unit main body 41 and a slider 42. Further, the operating unit main body 41 has a cap (not depicted) communicating with the lumen 31. The slider 42 is coupled to the operating unit main body 41 so as to be slidable in the direction of the longitudinal axis O1.

The catheter main body 3 is inserted into the sheath 2. The sheath 2 sheathes the catheter main body 3. The catheter main body 3 and the sheath 2 are configured to be able to move relative to each other along the direction of the longitudinal axis O1. The operating unit main body 41 is attached to the proximal end of the catheter main body 3. The slider 42 is attached to the proximal end of the sheath main body 21. Hence, the operating unit 4 can perform an operation of moving the sheath 2 and the catheter main body 3 relative to each other along the longitudinal axis O1 by sliding the slider 42 with respect to the operating unit main body 41. Specifically, the sheath 2 is moved to the proximal end side, or retreated, along the longitudinal axis O1 by moving the slider 42 to the proximal end side with respect to the operating unit main body 41. The sheath 2 is moved to the distal end side, or advanced, along the longitudinal axis O1 by moving the slider 42 to the distal end side with respect to the operating unit main body 41. An amount of movement of the slider 42 with respect to the operating unit main body 41 is set according to an amount of advancing or retreating movement of the sheath 2 with respect to the catheter main body 3.

Description will next be made of the endoscope 100 used in conjunction with the catheter 1. A configuration of the endoscope 100 is not particularly limited. The endoscope 100 is, for example, a publicly known side-viewing endoscope as depicted in FIG. 5. The endoscope 100 includes an operating unit 105 operated by an operator and an insertion portion 101 extended from the operating unit 105. The insertion portion 101 can be inserted into a body. The insertion portion 101 is flexible and is formed in a long length. A channel 102 is formed in the insertion portion 101. A distal end portion of the channel 102 communicates with an opening 104 disposed in a side surface of a distal end portion of the insertion portion 101. A raising base 103 is attached to the channel 102 within the distal end portion of the insertion portion 101. A raising base operating wire not depicted but extending to the operating unit 105 is connected to the raising base 103.

The operating unit 105 includes a knob 109 for a bending operation of the distal end portion of the insertion portion 101 and a lever (not depicted) that operates the raising base 103 via the raising base operating wire. In addition, the operating unit 105 is connected to a control device, a display device, a power supply, and the like, not depicted, via a universal cable 107.

A forceps plug 108 communicating with a proximal end portion of the channel 102 is disposed on a side portion of the operating unit 105. The catheter 1 can be inserted from the forceps plug 108 into the channel 102, and projected from the opening 104.

Description will next be made of an example of usage of the catheter 1 configured as described hereinbefore. In the following, a case of inserting the catheter 1 into a bile duct by using the rendezvous technique will be described as an example with reference to FIGS. 2 to 6.

First, an operator inserts a publicly known ultrasonic endoscope from a mouth of a patient into an alimentary canal. Next, a bile duct Bd is identified in an ultrasonic image, and a puncture needle inserted into a channel of the ultrasonic endoscope is inserted from the alimentary canal into an intrahepatic bile duct. A guide wire GW is inserted into the puncture needle. A distal end of the guide wire GW is inserted from the puncture needle into the bile duct Bd. The operator pushes forward the guide wire GW inserted in the bile duct Bd, and makes a distal end portion of the guide wire GW project from a duodenal papilla Dp into a duodenum D, as depicted in FIG. 5. Usually, when the guide wire GW is projected from the duodenal papilla Dp by a predetermined length, a loop is formed at the distal end portion of the guide wire GW. Thereafter, the ultrasonic endoscope and the puncture needle are extracted to the outside of the body while the distal end portion of the guide wire GW is placed within the duodenum D. At this time, a proximal end side of the guide wire GW is present on the outside of the body of the patient.

Next, the operator inserts the insertion portion 101 of the endoscope 100 from the mouth of the patient to the vicinity of the duodenal papilla Dp of the duodenum D. Incidentally, in an initial state in which the distal end portion of the catheter main body 3 is, in whole, inserted in the insertion hole 23 of the distal end member 22, the tapered portion 32 is elastically deformed and compressed by being pressed by the inner peripheral surface of the insertion hole 23.

Next, the catheter 1 is inserted into the channel 102 of the endoscope 100, and the catheter 1 is projected from the opening 104 at a distal end of the channel 102. Thereafter, the distal end portion of the catheter 1 is disposed in the vicinity of the guide wire GW while the guide wire GW projected from the duodenal papilla Dp to a duodenum D side is checked in an image of the endoscope 100. At this time, the raising base 103 is raised by an operation of the operating unit 105, so that the distal end portion of the catheter 1 is curved and directed toward a desired position.

Next, the operator holds the operating unit 4 of the catheter 1, and retreats the slider 42 with respect to the operating unit main body 41. As a result, the sheath 2 retreats in the direction of the longitudinal axis O1 with respect to the catheter main body 3, and the distal end portion of the catheter main body 3 projects from the distal end of the sheath 2. When the distal end portion of the catheter main body 3 projects from the distal end of the sheath 2, the external force on the tapered portion 32 compressed within the insertion hole 23 in the initial state described hereinbefore is released, and the distal end portion of the catheter main body 3 is restored to the opened state as depicted in FIG. 2. In such an opened state, the slit 5 is opened. The distal end portion of the catheter main body 3 in the opened state is brought closer to the guide wire GW, and the guide wire GW is inserted into the slit 5.

The circumferential position of the slit 5 in the catheter main body 3 is positioned so as to be a predetermined position with respect to the curving direction of the sheath 2 curved by the raising base 103. For example, a predetermined bending tendency is imparted to the catheter main body 3 and the sheath 2 in advance, and the slit 5 is formed in the curving direction according to the bending tendency. As a result, the slit 5 is positioned in the curving direction of the sheath 2 and the catheter main body 3 when the raising base 103 raises and curves the sheath 2. The guide wire GW can therefore be inserted into the slit 5 easily by an operation of making the distal end portion of the catheter main body 3 abut against the guide wire GW and pushing in the distal end portion of the catheter main body 3 in a state in which the distal end portion of the catheter main body 3 projects from the distal end member 22.

The slit 5 is formed in the outer peripheral surface of the catheter main body 3. Thus, the guide wire GW can be inserted into the slit 5 by bringing the outer peripheral surface side of the distal end portion of the catheter main body 3 closer to the guide wire GW. In addition, the guide wire GW can be inserted into the slit 5 such that the guide wire GW is along the outer peripheral surface side of the catheter main body 3. Further, because the slit 5 is formed along the longitudinal axis O1, the guide wire GW inserted inside the slit 5 can be held along the longitudinal axis O1.

Next, the operator performs an operation of advancing the slider 42 to the distal end side, and thereby advances the sheath 2 with respect to the catheter main body 3. As a result, in a state in which the guide wire GW is inserted in the slit 5, a proximal end portion of the tapered portion 32 is housed in the insertion hole 23 of the distal end member 22, and the tapered portion 32 is compressed and elastically deformed so as to reduce the opening width W1 of the slit 5. When the tapered portion 32 is elastically deformed in the state in which the guide wire GW is inserted in the slit 5, the guide wire GW is sandwiched by the closing of the slit 5, and the guide wire GW is held by the catheter 1. At this time, a part of the distal end side of the tapered portion 32 is in a state of projecting to the distal end side from the distal end member 22.

The operator pulls the proximal end side of the guide wire GW, which proximal end side is present outside the body of the patient, to the outside of the body. As depicted in FIG. 6, this operation draws in the guide wire GW, which is projected to the duodenum D, from the duodenal papilla Dp to the inside of the bile duct Bd. With this movement of the guide wire GW, the catheter 1 holding the guide wire GW is also drawn in from the duodenal papilla Dp to the inside of the bile duct Bd. At this time, the axis of the guide wire GW and the longitudinal axis O1 of the catheter 1 are substantially parallel with each other at the distal end portion of the catheter 1. The catheter 1 therefore advances from the duodenal papilla Dp to the inside of the bile duct Bd smoothly together with the guide wire GW.

After the catheter 1 is advanced to a treatment target site, the sheath 2 is retreated with respect to the catheter main body 3 again by an operation of retreating the slider 42. As a result, the distal end of the catheter main body 3 projects relative to the sheath 2, the tapered portion 32 is set in the opened state, and the holding of the guide wire GW is released. A predetermined treatment is thereafter performed by for example introducing a contrast medium into the inside of the bile duct Bd through the lumen 31 of the catheter 1.

The catheter 1 according to the present embodiment includes the catheter main body 3, the sheath 2, and the operating unit 4 that is disposed at the proximal end portion of the sheath 2 and moves the sheath 2 with respect to the catheter main body 3 along the longitudinal axis O1, the slit 5 extending along the longitudinal axis O1 from the distal end to the proximal end side is formed in the outer peripheral surface of the distal end portion of the catheter main body 3, and the outside diameter D4 of the distal end portion of the catheter main body 3 is larger than the inside diameter D2 of the insertion hole 23 of the distal end member 22. The catheter 1 is configured such that, in a state in which the distal end portion of the catheter main body 3 is housed in the distal end member 22, the distal end portion of the catheter main body 3 is elastically deformed by being pressed by the inner peripheral surface of the insertion hole 23 of the distal end member 22, and the opening width W1 of the slit 5 is smaller than when the distal end portion of the catheter main body 3 projects from the distal end of the sheath 2. In other words, the opening width W1 of the slit 5 can be changed according to relative movement of the catheter main body 3 and the sheath 2 in the direction of the longitudinal axis O1 by an operation of the operating unit 4. When the guide wire GW is to be inserted, the guide wire GW is inserted into the slit 5 easily because the opening width W1 of the slit 5 is wide. On the other hand, when the sheath 2 is advanced, the distal end portion of the catheter main body 3 is elastically deformed by being pressed from the outside, and the opening width W1 of the slit 5 is reduced, so that the guide wire GW can be held stably.

The slit 5 is formed in the outer peripheral surface of the catheter main body 3 so as to extend along the longitudinal axis O1. The guide wire GW can therefore be held along the longitudinal axis O1. As a result, the guide wire GW is held in a state in which the catheter 1 and the guide wire GW are in proximity to each other along the longitudinal axis O1, and the catheter 1 can be advanced from the duodenal papilla Dp to a treatment target site smoothly with the movement of the guide wire GW.

The catheter 1 according to the present embodiment has the tapered portion 32 at the distal end portion of the catheter main body 3. Due to this configuration, when the catheter main body 3 is housed in the distal end member 22 from a state in which the catheter main body 3 projects from the distal end of the distal end member 22, the distal end member 22 gradually presses the catheter main body 3. Thus, the distal end portion of the catheter main body 3 can be housed in the distal end member 22 smoothly. In addition, the sheath 2 can be advanced smoothly with respect to the catheter main body 3.

Second Embodiment

Figure 7A:
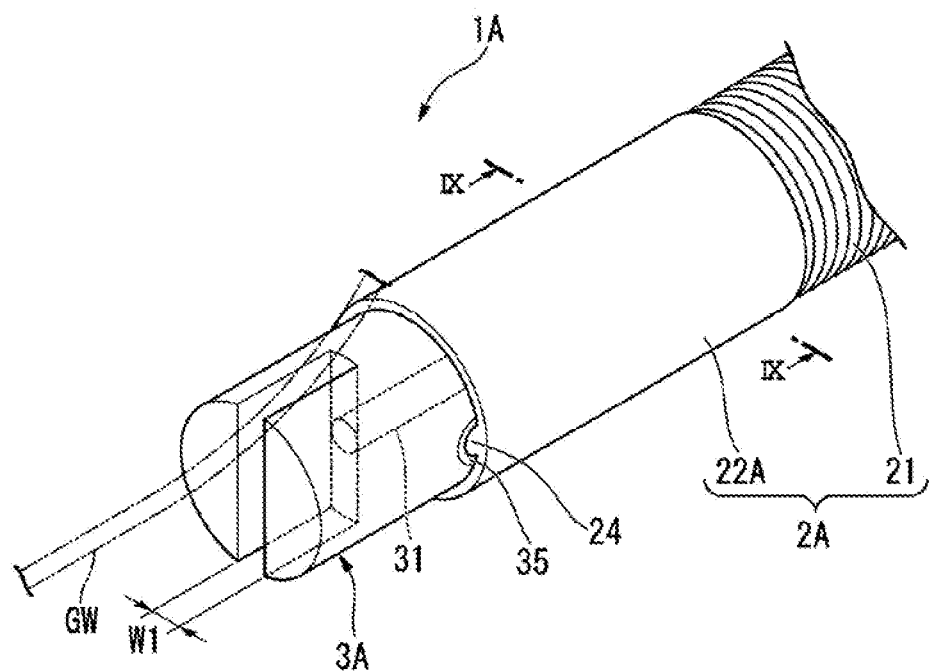
FIG. 7A is a perspective view of a distal end portion of a catheter according to a second embodiment.
Figure 7B:
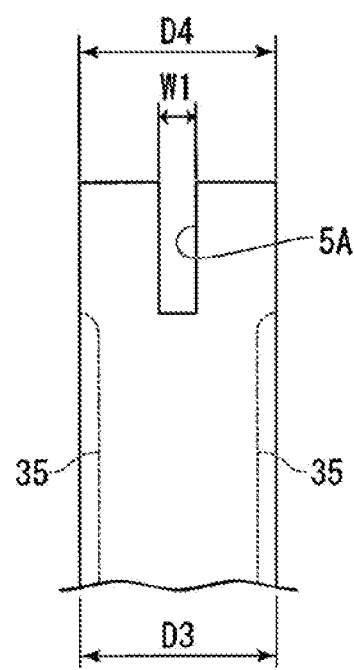
FIG. 7B is a side view of a catheter main body according to the second embodiment.
Figure 8:
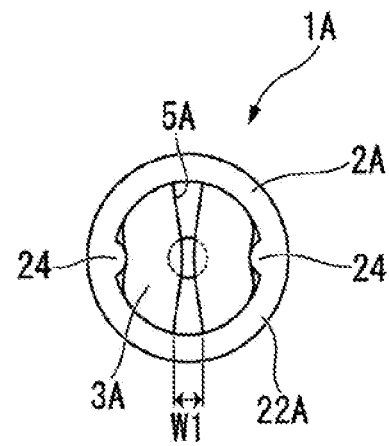
FIG. 8 is a view of the catheter according to the second embodiment as viewed from a distal end side.
Figure 9:
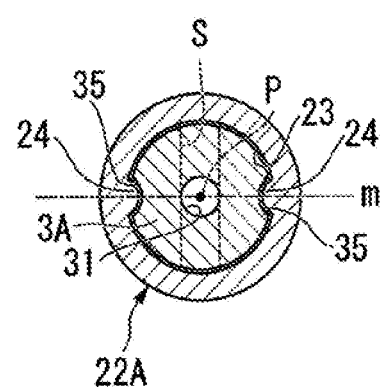
FIG. 9 is a sectional view taken along a line IX-IX of FIG. 7A.

A second embodiment of the disclosed technology will next be described with reference to FIGS. 7A to 9. FIG. 7A is a perspective view of a distal end portion of a catheter 1A according to the present embodiment. FIG. 7B is a side view of a catheter main body 3A. FIG. 8 is a view of the catheter 1A as viewed from a distal end side in a state in which the catheter main body 3A is, in whole, housed in a distal end member 22A. FIG. 9 is a sectional view taken along a line IX-IX of FIG. 7A. In the following description, parts having similar configurations to those of the catheter 1A according to the first embodiment are identified by the same numeral references, and detailed description thereof will be omitted.

Configurations of the distal end member and the catheter main body of the catheter 1A according to the present embodiment are different from those of the first embodiment. As depicted in FIG. 7A and FIG. 8, the distal end member 22A has a pair of protruding portions 24 within the insertion hole 23, the pair of protruding portions 24 projecting toward the center of the insertion hole 23. The protruding portions 24 are formed so as to extend in the direction of the longitudinal axis O1 over an entire length of the distal end member 22A. As depicted in FIG. 9, the pair of protruding portions 24 is disposed on a straight line m passing through a center point P of the insertion hole 23 of the distal end member 22A such that the protruding portions 24 are opposed to each other.

As depicted in FIG. 7B, in the catheter main body 3A, the outside diameter D4 of a distal end is substantially equal to the outside diameter D3 on a proximal end side. A slit 5A is formed so as to cross in a position passing through the center point P of the catheter main body 3A and divide the catheter main body 3A into two parts. A pair of recessed grooves 35, or a pair of recessed portions, is formed in the outer peripheral surface of the catheter main body 3A on a proximal end side as compared to the slit 5A. As depicted in FIG. 9, the recessed grooves 35 are formed so as to conform to the shape of the protruding portions 24. Each of the pair of recessed grooves 35 is disposed on the straight line m passing through the center point P of the catheter main body 3A. In FIG. 9, the position of the slit 5A disposed on the distal end side of the catheter main body 3A is indicated by a broken line. As viewed in the direction of the longitudinal axis O1, the straight line m is substantially orthogonal to a direction in which the slit 5A is formed. As depicted in FIG. 7B, the recessed grooves 35 are formed such that end portions on the distal end side of the recessed grooves 35 are decreased in groove depth toward the distal end side.

In a state in which the protruding portions 24 are inserted in the recessed grooves 35, the catheter main body 3A and a sheath 2A move relative to each other in the direction of the longitudinal axis O1. At this time, the protruding portions 24 are guided by the recessed grooves 35, so that relative rotation between the catheter main body 3A and the sheath 2A is restricted. The slit 5A can therefore be positioned in a circumferential direction more reliably.

The distal ends of the recessed grooves 35 are located on the proximal end side as compared to the slit 5A, and thus, no recessed portion is formed in a distal end portion of the catheter main body 3A. Therefore, in the distal end portion of the catheter main body 3A, the diameter of the catheter main body 3A on the straight line m is larger than a distance between the pair of protruding portions 24. Hence, as depicted in FIG. 8, in a state in which the distal end portion of the catheter main body 3A is, in whole, housed in the distal end member 22A, the distal end portion of the catheter main body 3A is elastically deformed by being pressed by the pair of protruding portions 24, and an opening width W1 of the slit 5A is reduced. Incidentally, because the protruding portions 24 are located on the straight line m, the distal end portion of the catheter main body 3 is elastically deformed easily in a direction of reducing the opening width W1 of the slit 5A.

On the other hand, as depicted in FIG. 7A, when the distal end portion of the catheter main body 3A projects to the distal end side from the distal end member 22A, the catheter main body 3A is released from the pressing by the protruding portions 24. Thus, the slit 5A has the original opening width W1, and the guide wire GW can easily be inserted into the slit 5A.

When the sheath 2 is advanced in a state in which the guide wire GW is inserted in the slit 5A, the distal end portion of the catheter main body 3A is elastically deformed by being pressed in a central direction by the protruding portions 24 of the distal end member 22A. When the distal end portion of the catheter main body 3A is elastically deformed in a state in which the guide wire GW is inserted in the slit 5A, the guide wire GW is sandwiched by the slit 5A, and the guide wire GW is held by the catheter 1A. At this time, a part of the distal end side of the catheter main body 3A is in a state of projecting to the distal end side from the distal end member 22A. When the guide wire GW is thus inserted into the slit 5A from an outer peripheral surface side of the catheter main body 3 and held within the slit 5A, the axis of the guide wire GW and the longitudinal axis O1 of the catheter 1 are substantially parallel with each other at the distal end portion of the catheter 1A as in the first embodiment. The catheter 1 can therefore be advanced smoothly from the duodenal papilla Dp to the inside of the bile duct Bd together with the guide wire GW.

In the first embodiment, an example has been illustrated in which the catheter main body 3 has the tapered portion 32 having a larger diameter than the inside diameter D2 of the insertion hole 23 of the distal end member 22, and the tapered portion 32 is pressed by the inner peripheral surface of the insertion hole 23. On the other hand, the catheter 1A according to the present embodiment is configured such that the protruding portions 24 on the inner peripheral surface of the distal end member 22A press and elastically deform the catheter main body 3A, and reduce the opening width W1 of the slit 5A. When a maximum outside diameter in the distal end portion of the catheter main body is thus larger than a minimum inside diameter in the distal end portion of the sheath, the opening width of the slit 5A can be reduced.

Hence, the catheter 1A according to the present embodiment produces effects similar to those of the catheter 1 according to the first embodiment.

Also in the present embodiment, the distal end portion of the catheter main body 3A may have a tapered portion as in the first embodiment.

In addition, while an example has been illustrated in which two protruding portions 24 are disposed on the inner peripheral surface of the distal end member 22A, there may be only one protruding portion as long as the distal end portion of the catheter main body 3A is pressed and elastically deformable by the protruding portion 24 in a state in which the distal end portion of the catheter main body 3A is housed in the sheath 2A.

In a case where one protruding portion is formed on the inner peripheral surface of the sheath, it suffices to form the protruding portion such that a distance between the inner surface of the sheath, which inner surface is opposed to the protruding portion, and the distal end of the protruding portion is smaller than the diameter of the distal end portion of the long-axis member, in the distal end portion of the sheath.

In a case where a plurality of protruding portions are formed on the inner peripheral surface of the sheath, it suffices to form the protruding portions such that distances between the distal ends of the plurality of protruding portions in directions orthogonal to the longitudinal axis are smaller than the diameter of the distal end portion of the long-axis member.

Preferred embodiments of the disclosed technology have been described hereinbefore. However, the disclosed technology is not limited to these embodiments. Addition, omission, and replacement of configurations and other changes can be made without departing from the spirit of the disclosed technology.

Figure 10:
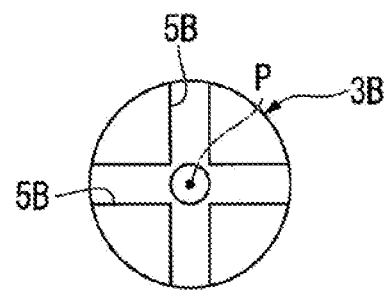
FIG. 10 is a view of a modification of a slit of the catheter main body as viewed from a distal end side.

The slit formed in the catheter main body is not particularly limited as long as the slit is formed in the outer peripheral surface of the distal end portion of the catheter main body so as to extend from the distal end to the proximal end side along the longitudinal axis O1. For example, FIG. 10 is a diagram depicting a modification of the catheter main bodies 3 and 3A according to the first embodiment and the second embodiment, and is a view of a catheter main body as viewed from a distal end side. As depicted in FIG. 10, two slits 5B passing through the center point P of a catheter main body 3B and intersecting each other in orthogonal directions may be formed. In addition, as with the slit 5A according to the second embodiment, the slit 5 according to the first embodiment may be formed so as to penetrate in a diametrical direction of the catheter main body 3.

In the foregoing embodiments, an example has been illustrated in which the slit and the lumen communicate with each other in a radial direction of the catheter main body. However, the configuration in which the slit communicates with the lumen is not essential. For example, a configuration may be adopted in which the slit in a state of not communicating with the lumen is formed on the outside in the radial direction of the lumen, and there is a wall portion between the lumen and the slit. In the case of such a slit, in a state in which the slit holds a first guide wire, another wire or a treatment instrument can be projected from the lumen.

In the foregoing embodiments, an example of the sheath having the distal end member at the distal end of the coil sheath has been illustrated. However, the form of the sheath is not limited to this. For example, the sheath may be formed of a resin over the entire length of the sheath. In addition, while an example is cited in which the sheath main body is a coil sheath in the foregoing embodiments, the form of the sheath is not limited to this. For example, the sheath main body may be flexible and formed of a resin. In a case where the sheath is formed of a resin, a resin such as PTFE can be adopted, for example.

In the foregoing embodiments, an example has been illustrated in which a part of the distal end portion of the catheter main body projects from the distal end of the sheath when the guide wire GW is held by the catheter. However, the disclosed technology is not limited to this configuration.

Figure 11:
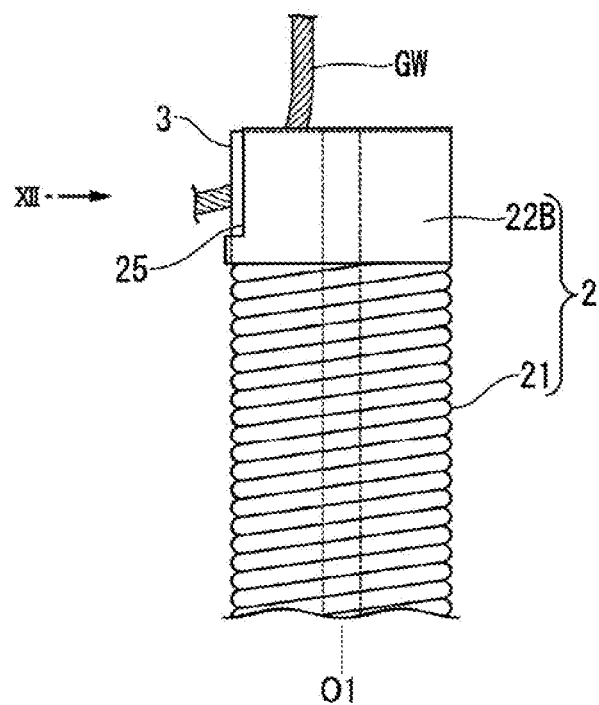
FIG. 11 is a side view depicting a modification of a sheath.
Figure 12:
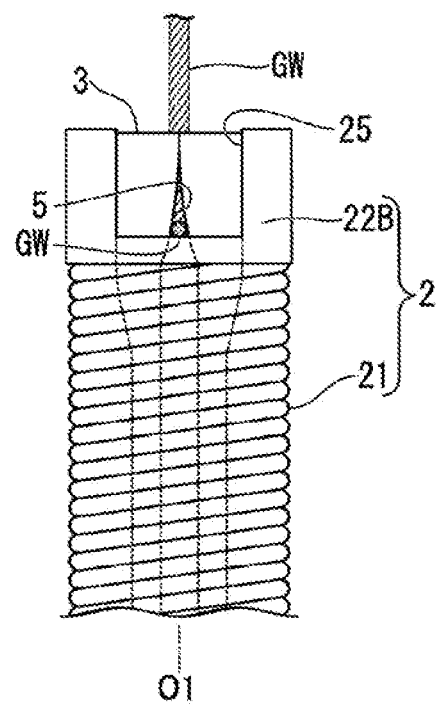

FIG. 11 and FIG. 12 are side views depicting a modification of the distal end member 22 of the sheath 2 according to the first embodiment. FIG. 12 is a side view as viewed from the direction of an arrow XII depicted in FIG. 11. An opening 25 is formed in a part in the circumferential direction of a distal end member 22B according to the present modification, the opening 25 penetrating in a thickness direction from the outer peripheral surface to the insertion hole 23, or the inner peripheral surface, of the distal end member 22B, and extending from the distal end of the distal end member 22B along the longitudinal axis O1. The opening 25 and the slit 5 are arranged such that the positions of the opening 25 and the slit 5 coincide with each other in the circumferential direction of the distal end member 22B. Therefore, as depicted in FIG. 11, when the catheter main body 3 is housed in the distal end member 22B and holds the guide wire GW, the guide wire GW is prevented from interfering with the distal end member 22B. Because the distal end member 22B has the opening 25, the sheath 2 can be advanced to the distal end of the catheter main body 3B (the distal end portion of the catheter main body 3B can be housed in the sheath 2) in a state in which the guide wire GW is held within the slit 5. A catheter 1B having such a configuration can hold the guide wire GW more securely. Incidentally, the distal end member 22B according to the present modification is also applicable in the second embodiment.

Figure 13:
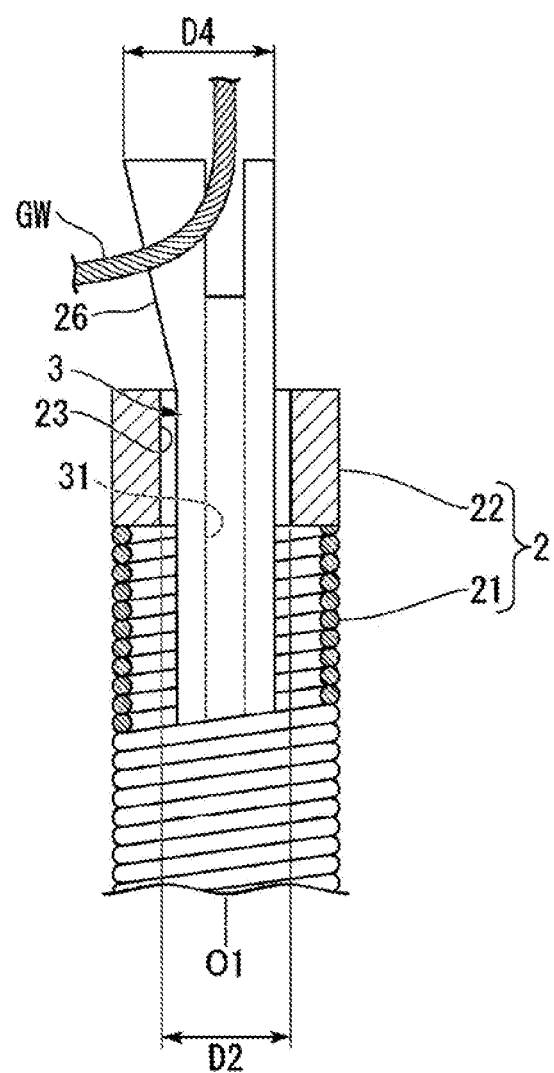
FIG. 13 is a fragmentary sectional view depicting a modification of the catheter according to the first embodiment.

A method of making the outside diameter D4 of the distal end portion of the catheter main body larger than the inside diameter D2 of the distal end member of the sheath is not limited to the foregoing embodiments. For example, as depicted in FIG. 13, an inclined portion 26 inclined with respect to the longitudinal axis O1 from the proximal end side to the distal end of the catheter main body 3 may be formed in at least a part of the distal end portion of the catheter main body 3 in the circumferential direction. Even when such a configuration is adopted, the outside diameter D4 of the distal end of the catheter main body 3 becomes larger than the inside diameter D2 of the insertion hole 23, or the inside diameter of the distal end member 22. As a result, when the distal end portion of the catheter main body 3 is housed in the insertion hole 23 of the distal end member 22, the distal end portion of the catheter main body 3 is elastically deformed by being pressed by the inner peripheral surface of the insertion hole 23, and the opening width W1 of the slit 5 is reduced. Even such a configuration produces effects similar to those of the first embodiment.

Figure 14:
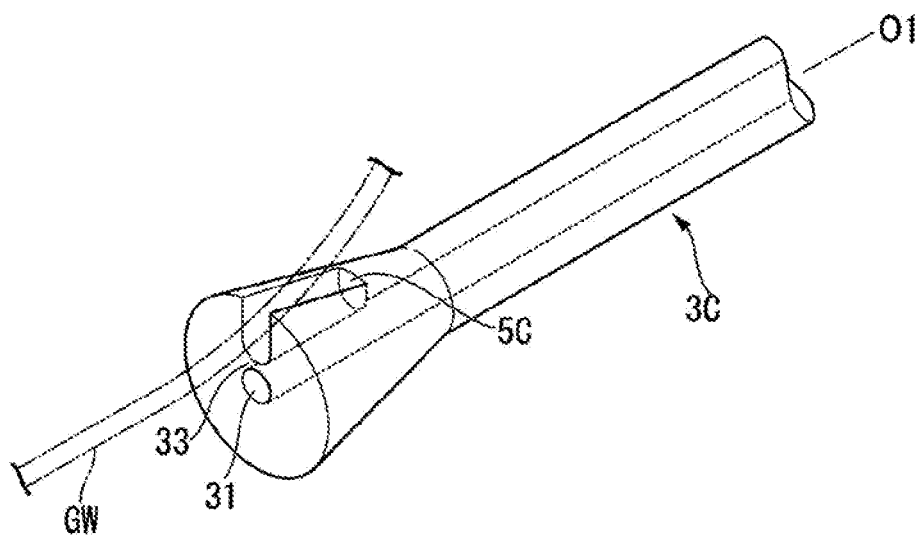
FIG. 14 is a perspective view depicting a distal end portion of a catheter according to a modification of the first embodiment.
Figure 15:
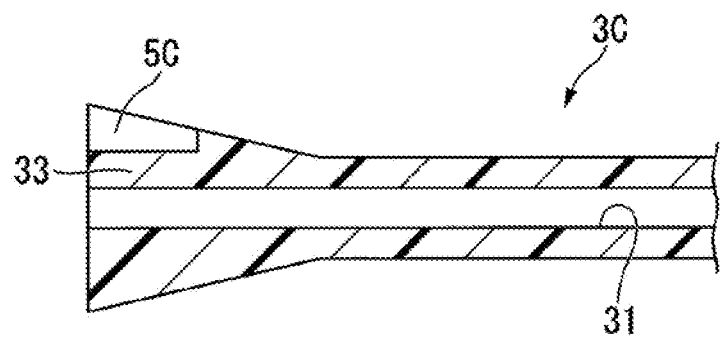
FIG. 15 is a sectional view taken in a direction along a longitudinal axis of a catheter main body 3C according to the present modification.

FIG. 14 is a perspective view depicting a distal end portion of a catheter main body 3C according to a modification of the first embodiment. FIG. 15 is a sectional view taken in a direction along the longitudinal axis of the catheter main body 3C according to the present modification. As in the modification depicted in FIG. 14 and FIG. 15, the catheter main body 3C may be of a configuration such that the catheter main body 3C has a division wall 33 between a slit 5C and the lumen 31, and the slit 5C does not communicate with the lumen 31. When the configuration is adopted in which the slit 5C does not communicate with the lumen 31, the lumen 31 is not closed by the guide wire GW and the functions of the lumen 31 are not hindered even in a state in which the guide wire GW is held in the slit 5C. As a result, in the state of holding the guide wire GW, the catheter main body 3C allows another guide wire (not depicted) to be inserted through the lumen 31, or allows a contrast medium to be fed through the lumen 31.

In the foregoing embodiments, a configuration has been illustrated in which the sheath is moved relative to the catheter main body by an operation of the operating unit. However, it suffices for the operating unit to have a configuration that moves the sheath and the catheter main body relative to each other along the longitudinal axis. For example, a configuration may be adopted in which the catheter main body is moved relative to the sheath along the longitudinal axis by an operation of the operating unit.

According to the foregoing embodiments of the disclosed technology, it is possible to provide a catheter that can easily be introduced into a hollow organ by the rendezvous technique.

In sum, one aspect of the disclosed technology is directed to a catheter comprises a catheter main body having a longitudinal axis. A sheath covers the catheter main body and is movable along the longitudinal axis with respect to the catheter main body. An operating unit is disposed at a proximal end portion of the sheath. The operating unit is used to move the sheath and the catheter main body with respect to one another along the longitudinal axis. The catheter main body includes a slit that is formed in an outer peripheral surface of a distal end portion thereof. The slit extends along the longitudinal axis from a slit distal end to a slit proximal end side. In a direction of the longitudinal axis, the distal end of the catheter main body and the distal end of the slit coincides with one another. An outside diameter of the distal end portion of the catheter main body is larger than an inside diameter of a distal end portion of the sheath in a state in which the distal end portion of the catheter main body is housed in the sheath. The distal end portion of the catheter main body is elastically deformed by being pressed by an inner peripheral surface of the sheath. An opening width of the slit is smaller than the opening width of the slit in a state in which the distal end portion of the catheter main body projects from the distal end of the sheath.

The catheter main body includes a tapered portion formed in the distal end portion thereof and wherein the tapered portion is increased in diameter from the proximal end side to the distal end. The tapered portion is formed in at least a part in a circumferential direction of an outer peripheral surface of the catheter main body. The tapered portion includes an outside diameter located between a proximal end of the slit and the distal end of the slit, which is larger than an inside diameter in the distal end of the sheath. The sheath includes an opening being communicated with an inner peripheral surface and an outer peripheral surface thereof and extending along the longitudinal axis from the distal end of the sheath that is formed in a part in a circumferential direction of the distal end portion of the sheath. A lumen is formed by communicating from the distal end of the catheter main body to a proximal end of the catheter main body.

Another aspect of the disclosed technology is directed to a catheter comprises a catheter main body having a longitudinal axis. A sheath covers the catheter main body and is movable along the longitudinal axis with respect to the catheter main body. An operating unit is disposed at a proximal end portion of the sheath and the operating unit is used to move the sheath and the catheter main body relative to one another along the longitudinal axis. The catheter main body includes a slit being formed in an outer peripheral surface of a distal end portion thereof. The slit extends along the longitudinal axis from a slit distal end to a slit proximal end side. In a direction of the longitudinal axis, the distal end of the catheter main body and the distal end of the slit coincides with one another. At least one of protruding portion is disposed on a part of an inner peripheral surface of the distal end portion of the sheath and in a state in which the distal end portion of the catheter main body is housed in the sheath, the distal end portion of the catheter main body is elastically deformed by being pressed by the protruding portion, and an opening width of the slit being smaller than the opening width of the slit in a state in which the distal end portion of the catheter main body projects from the distal end of the sheath.

The catheter main body includes a recessed portion formed in an outer peripheral surface positioned on a proximal end side of the slit and the protruding portion is formed so as to be slidable in the recessed portion. In the distal end portion of the sheath, a distance between an inner surface of the sheath, the inner surface is opposed to the protruding portion and a top of the protruding portion is smaller than a diameter of the distal end portion of the catheter main body. A distance between distal ends of the protruding portions in a direction orthogonal to the longitudinal axis is smaller than a diameter of the distal end portion of the catheter main body. The sheath includes an opening being communicated with an inner peripheral surface and an outer peripheral surface thereof and extending along the longitudinal axis from the distal end of the sheath that is formed in a part in a circumferential direction of the distal end portion of the sheath.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A catheter comprising:
    a catheter main body having a longitudinal axis;
    a sheath that covers the catheter main body and being configured to move along the longitudinal axis with respect to the catheter main body;
    an operating unit disposed at a proximal end portion of the sheath, the operating unit being used to move the sheath and the catheter main body with respect to one another along the longitudinal axis; wherein:
        the catheter main body includes a slit being formed in an outer peripheral surface of a distal end portion of the catheter main body, and a lumen configured to allow communication between the distal end portion of the catheter main body and a proximal end of the catheter main body,
        the slit extends along the longitudinal axis from the outer peripheral surface of the catheter main body to a central axis of the catheter main body,
        the slit extends below the central axis of the catheter main body and terminates at an inner surface of the lumen such that the slit extends in a cross-section orthogonal to the longitudinal axis,
        in a direction of the longitudinal axis, the distal end portion of the catheter main body and a distal end of the slit coincides with one another,
        an outside diameter of the distal end portion of the catheter main body being larger than an inside diameter of a distal end portion of the sheath,
        in a state in which the distal end portion of the catheter main body is housed in the sheath, the distal end portion of the catheter main body being elastically deformed by being pressed by an inner peripheral surface of the sheath, and an opening width of the slit being smaller than the opening width of the slit in a state in which the distal end portion of the catheter main body projects from the distal end portion of the sheath, and
        the catheter main body is configured to hold a guide wire in the slit such that when the guide wire is positioned in the catheter main body, an axis of the guide wire and the longitudinal axis of the catheter main body are parallel to each other.

2. The catheter of claim 1, wherein the catheter main body includes a tapered portion formed in the distal end portion of the catheter main body and wherein the tapered portion is increased in diameter from a proximal end portion of the catheter main body to the distal end portion of the catheter main body.

3. The catheter of claim 2, wherein the tapered portion is formed by the outer peripheral surface of the catheter main body.

4. The catheter of claim 3, wherein the tapered portion includes an outside diameter located between a proximal end of the slit and the distal end of the slit, which is larger than the inside diameter in the distal end portion of the sheath.

5. The catheter of claim 1, wherein the sheath includes an opening configured to communicate with the inner peripheral surface and an outer peripheral surface of the sheath, and the opening extends circumferentially around at least a portion of the distal end portion of the sheath.

6. The catheter of claim 1, wherein
    an insertion hole is formed in the sheath, the insertion hole communicates with the inner peripheral surface and an outer surface of the sheath, and the insertion hole extends from the distal end portion of the sheath along the longitudinal axis,
    in a state in which the distal end portion of the catheter main body is protruded from the distal end portion of the sheath, the slit is configured to accommodate the guide wire,
    when the distal end portion of the catheter main body is housed into the sheath, the catheter main body is configured to hold the guide wire in the slit such that the axis of the guide wire and the longitudinal axis of the catheter main body are parallel to each other.

7. The catheter of claim 1, wherein
    in a state in which the distal end portion of the catheter main body is housed in the sheath, the distal end portion of the catheter main body is elastically deformed such that edges of the slit are in a non-overlap state in a circumferential direction, or the distal end portion of the catheter main body is elastically deformed such that edges of the slit are positioned side by side in a circumferential direction.

8. The catheter of claim 1, wherein
    the lumen is elongated along the longitudinal axis and opened at the distal end portion of the catheter main body,
    an opening width of the slit in a circumferential direction is substantially parallel with a diameter of the lumen.

* * * * *